United States Patent
Abe et al.

(10) Patent No.: US 12,232,847 B2
(45) Date of Patent: Feb. 25, 2025

(54) WAVELENGTH CONVERTER; AND LIGHT EMITTING DEVICE, MEDICAL SYSTEM, ELECTRONIC APPARATUS, AND INSPECTION METHOD USING SAME

(71) Applicant: Panasonic Intellectual Property Management Co., Ltd., Osaka (JP)

(72) Inventors: Takeshi Abe, Osaka (JP); Shozo Oshio, Osaka (JP); Mitsuru Nitta, Kyoto (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 521 days.

(21) Appl. No.: 17/604,419

(22) PCT Filed: Feb. 19, 2020

(86) PCT No.: PCT/JP2020/006524
§ 371 (c)(1),
(2) Date: Oct. 17, 2021

(87) PCT Pub. No.: WO2020/217671
PCT Pub. Date: Oct. 29, 2020

(65) Prior Publication Data
US 2022/0175250 A1 Jun. 9, 2022

(30) Foreign Application Priority Data

Apr. 24, 2019 (JP) .................................. 2019-082925

(51) Int. Cl.
*H01S 5/00* (2006.01)
*A61B 5/00* (2006.01)
(Continued)

(52) U.S. Cl.
CPC ............ *A61B 5/0071* (2013.01); *A61N 5/062* (2013.01); *A61N 5/067* (2021.08);
(Continued)

(58) Field of Classification Search
CPC ... A61B 5/0071; A61B 2503/40; A61B 1/042; A61B 1/043; A61B 1/0638;
(Continued)

(56) References Cited

U.S. PATENT DOCUMENTS

2006/0082679 A1 4/2006 Chua
2006/0082995 A1 4/2006 Chua
(Continued)

FOREIGN PATENT DOCUMENTS

EP 3904488 A1 11/2021
JP 2006-114911 A 4/2006
(Continued)

OTHER PUBLICATIONS

Extended European Search Report for corresponding EP Application No. 20794989.2 dated Jun. 7, 2022.
(Continued)

*Primary Examiner* — Michelle Mandala
*Assistant Examiner* — Jordan M Klein
(74) *Attorney, Agent, or Firm* — Renner, Otto, Boisselle & Sklar, LLP

(57) ABSTRACT

A wavelength converter includes a first phosphor activated with $Cr^{3+}$; and a second phosphor activated with at least one ion of $Ce^{3+}$ or $Eu^{2+}$. A fluorescence spectrum of a fluorescence emitted by the second phosphor has a peak where a fluorescence intensity shows a maximum value in a wavelength range of 500 nm or more to less than 580 nm. The wavelength converter emits a fluorescence having a light component over an entire range of 500 nm or more to less than 580 nm. The wavelength converter emits a light having a spectrum in which a ratio of a minimum light emission intensity to a maximum light emission intensity is 40% or less in a wavelength range of 550 nm or more to 700 nm or less.

17 Claims, 7 Drawing Sheets

(51) Int. Cl.
*A61N 5/06* (2006.01)
*A61N 5/067* (2006.01)
*C09K 11/77* (2006.01)

(52) U.S. Cl.
CPC ...... *C09K 11/7708* (2013.01); *C09K 11/7774* (2013.01); *C09K 11/7776* (2013.01); *H01S 5/0087* (2021.01); *A61B 2503/40* (2013.01); *A61N 2005/0663* (2013.01)

(58) Field of Classification Search
CPC ...... A61B 1/0653; A61N 5/062; A61N 5/067; C09K 11/7708; C09K 11/7774; C09K 11/7776; H01L 33/504; H01L 25/167
See application file for complete search history.

(56) References Cited

U.S. PATENT DOCUMENTS

| | | | |
|---|---|---|---|
| 2016/0287081 A1 | 10/2016 | Yang | |
| 2017/0343188 A1* | 11/2017 | Oshio | ............ F21K 9/64 |
| 2018/0120157 A1 | 5/2018 | Kaufmann | |
| 2018/0358514 A1 | 12/2018 | Tragl | |
| 2019/0088832 A1 | 3/2019 | Onuma | |
| 2020/0048549 A1 | 2/2020 | Hong | |

FOREIGN PATENT DOCUMENTS

| | | | |
|---|---|---|---|
| JP | 2007-17986 A | 1/2007 | |
| JP | 2018-515913 A | 6/2018 | |
| JP | 2018-518046 A | 7/2018 | |
| JP | 6461411 B1 | 1/2019 | |
| WO | 2012/069542 A1 | 5/2012 | |
| WO | 2017/164214 A1 | 9/2017 | |
| WO | 2018/143198 A1 | 8/2018 | |
| WO | 2018/207703 A1 | 11/2018 | |
| WO | WO-2019063309 A1 * | 4/2019 | ........... C09K 11/645 |

OTHER PUBLICATIONS

International Search Report for corresponding Application No. PCT/JP2020/006524, mailed Apr. 28, 2020.
Written Opinion for corresponding Application No. PCT/JP2020/006524, mailed Apr. 28, 2020.
Search Report for corresponding Chinese Patent Application No. 202080029694.5 issued May 28, 2024, with English machine translation.

* cited by examiner

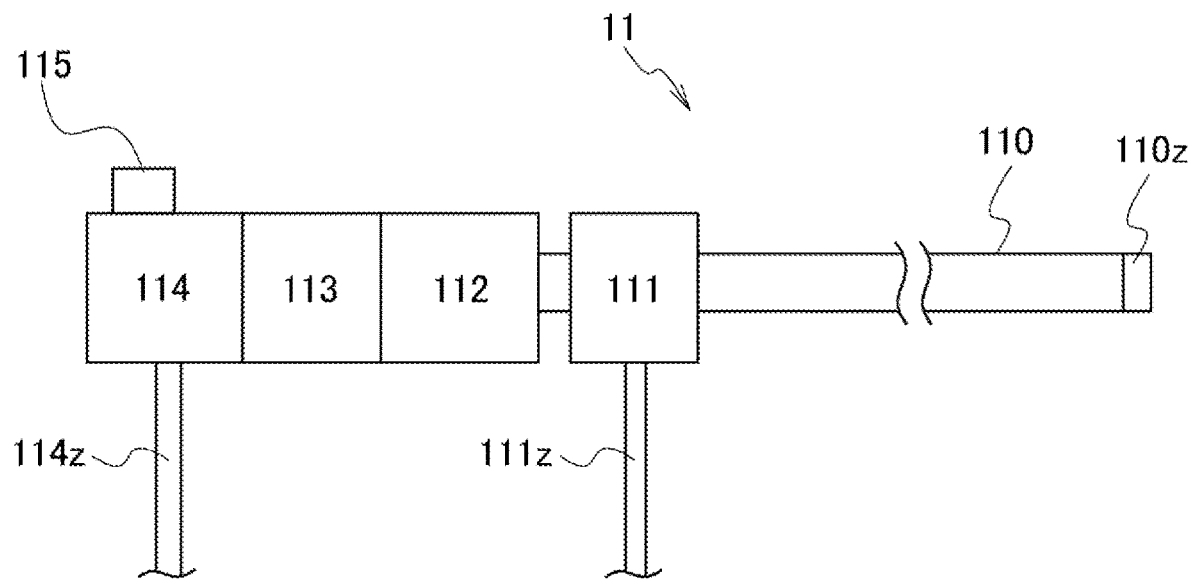

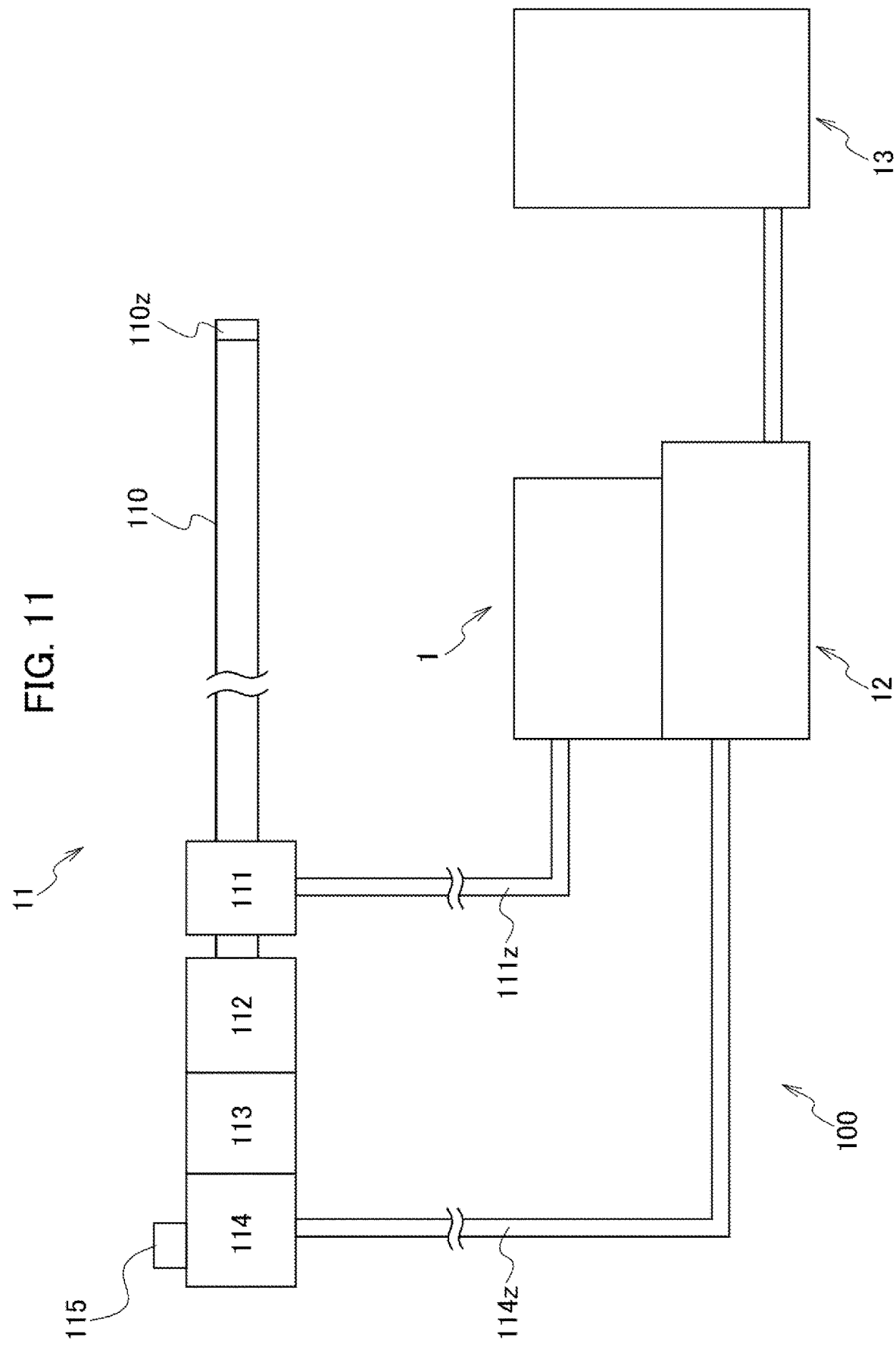

WAVELENGTH CONVERTER; AND LIGHT EMITTING DEVICE, MEDICAL SYSTEM, ELECTRONIC APPARATUS, AND INSPECTION METHOD USING SAME

TECHNICAL FIELD

The present invention relates to a wavelength converter, and a light emitting device, a medical system, an electronic apparatus, and an inspection method using the wavelength converter.

BACKGROUND

A method of observing lesions, called a fluorescence imaging method, has been attracting attention recently in the medical field. The fluorescence imaging method is a method of observing a lesion by administering a fluorescent drug that selectively binds to the lesion such as a tumor to a subject, exciting the fluorescent drug with a specific light, and detecting and imaging fluorescence emitted from the fluorescent drug by an image sensor. The fluorescence imaging method makes it possible to observe lesions that are difficult to observe visually.

As a typical fluorescence imaging method, a fluorescence imaging method (ICG fluorescence method) using indocyanine green (ICG) as a fluorescent drug is known. The ICG is excited by a near-infrared light (for example, fluorescence peak wavelength is 770 nm), which easily penetrates a living body, and emits a near-infrared light of a longer wavelength (for example, fluorescence peak wavelength is 810 nm). Therefore, by detecting the fluorescence emitted from the ICG, observation of a lesion inside the living body is possible. The ICG fluorescence method is a minimally invasive medical technology that achieves the observation of lesions inside the living body without damaging the living body.

The fluorescence imaging method, such as the ICG fluorescence method, uses at least a device that emits a near-infrared light. As an optoelectronic element emitting near-infrared fluorescence, Patent Literature 1 discloses an optoelectronic element that includes a semiconductor chip emitting a primary beam and a conversion material including $Cr^{3+}$ ions and/or $Ni^{2+}$ ions.

CITATION LIST

Patent Literature

PTL1: Japanese Translation of PCT International Application Publication No. JP-T-2018-518046
PTL2: WO 2017/164214

SUMMARY

As described above, to utilize a fluorescence imaging method, such as the ICG fluorescence method, at least a device for emitting near-infrared light is used. In contrast, to normally visually observe the state of a mucosal surface layer through an image projected by an image sensor for visible light or through a lens, it is preferable that visible light is also emitted. Therefore, if a device for simultaneously emitting visible light and near-infrared light is provided, it is possible to achieve both normal observation using visible light and special observation using near-infrared light.

Patent Literature 2 is known as a device for simultaneously emitting visible light and near-infrared light. Patent Literature 2 discloses a light source device that combines a deep red phosphor emitting a fluorescence including a near-infrared fluorescent component, a phosphor emitting a fluorescence having a wavelength different from that of the deep red phosphor, and a light emitting device.

However, in the fluorescence spectrum of fluorescence emitted by such a conventional device, the fluorescence component of visible light and the fluorescence component of near-infrared light are not sufficiently separated, and the light emission intensity of deep red light, which becomes noise of an image sensor for near-infrared light, becomes relatively high as an issue. Therefore, when normal observation and special observation are simultaneously performed using such a conventional device, the contrast of the fluorescence imaging image obtained becomes low as an issue.

The present invention has been made in consideration of such issues as described above. It is an object of the present invention to provide a wavelength converter capable of emitting a fluorescence spectrum in which a fluorescent component of visible light and a fluorescent component of near-infrared light are sufficiently separated and in which the light emission intensity of deep red light is relatively low, and a light emitting device, a medical system, an electronic apparatus, and an inspection method using the wavelength converter.

In response to the above issues, a wavelength converter according to a first aspect of the present invention includes: a first phosphor activated with $Cr^{3+}$; and a second phosphor activated with at least one ion of $Ce^{3+}$ or $Eu^{2+}$. A fluorescence spectrum of a fluorescence emitted by the second phosphor has a peak where a fluorescence intensity shows a maximum value in a wavelength range of 500 nm or more to less than 580 nm. The wavelength converter emits a fluorescence having a light component over an entire range of 500 nm or more to less than 580 nm. The wavelength converter emits a light having a spectrum in which a ratio of a minimum light emission intensity to a maximum light emission intensity is 40% or less in a wavelength range of 550 nm or more to 700 nm or less.

A light emitting device according to a second aspect of the present invention includes: the wavelength converter according to the first aspect, and a light source configured to emit a light to be wavelength-converted by the wavelength converter.

A medical system according to a third aspect of the present invention includes the light emitting device according to the second aspect.

An electronic apparatus according to a fourth aspect of the present invention includes the light emitting device according to the first aspect.

An inspection method according to a fifth aspect of the present invention uses the light emitting device according to the first aspect.

BRIEF DESCRIPTION OF DRAWINGS

FIG. 9 is a schematic diagram illustrating a configuration of an endoscope according to the present embodiment.

FIG. 10 is a schematic diagram illustrating an example of an image sensor.

FIG. 11 is a schematic diagram illustrating a configuration of an endoscope system according to the present embodiment.

DESCRIPTION OF EMBODIMENTS

Figure 1:
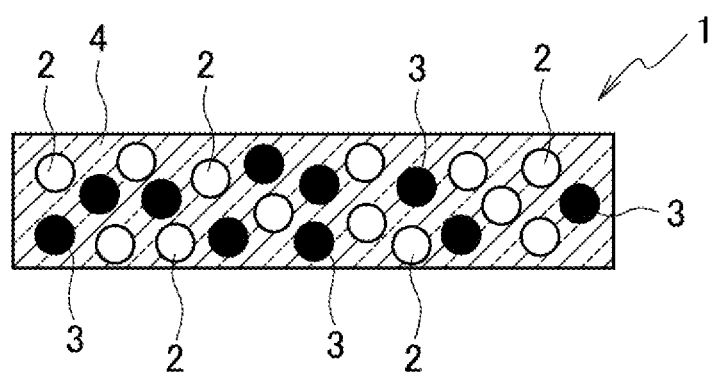
FIG. 1 is a schematic sectional view of an example of a wavelength converter according to a present embodiment.

A detailed description is given below of a wavelength converter, and a light emitting device, a medical system, an electronic apparatus, and an inspection method using the wavelength converter according to a present embodiment. Note that dimensional ratios in the drawings are exaggerated for convenience of explanation, and are sometimes different from actual ratios.

[Wavelength Converter]

As illustrated in FIG. 1, a wavelength converter 1 according to the present embodiment includes a first phosphor 2 and a second phosphor 3. The first phosphor 2 is a phosphor activated with $Cr^{3+}$. The second phosphor 3 is a phosphor activated with at least one ion of $Ce^{3+}$ or $Eu^{2+}$.

Figure 2:
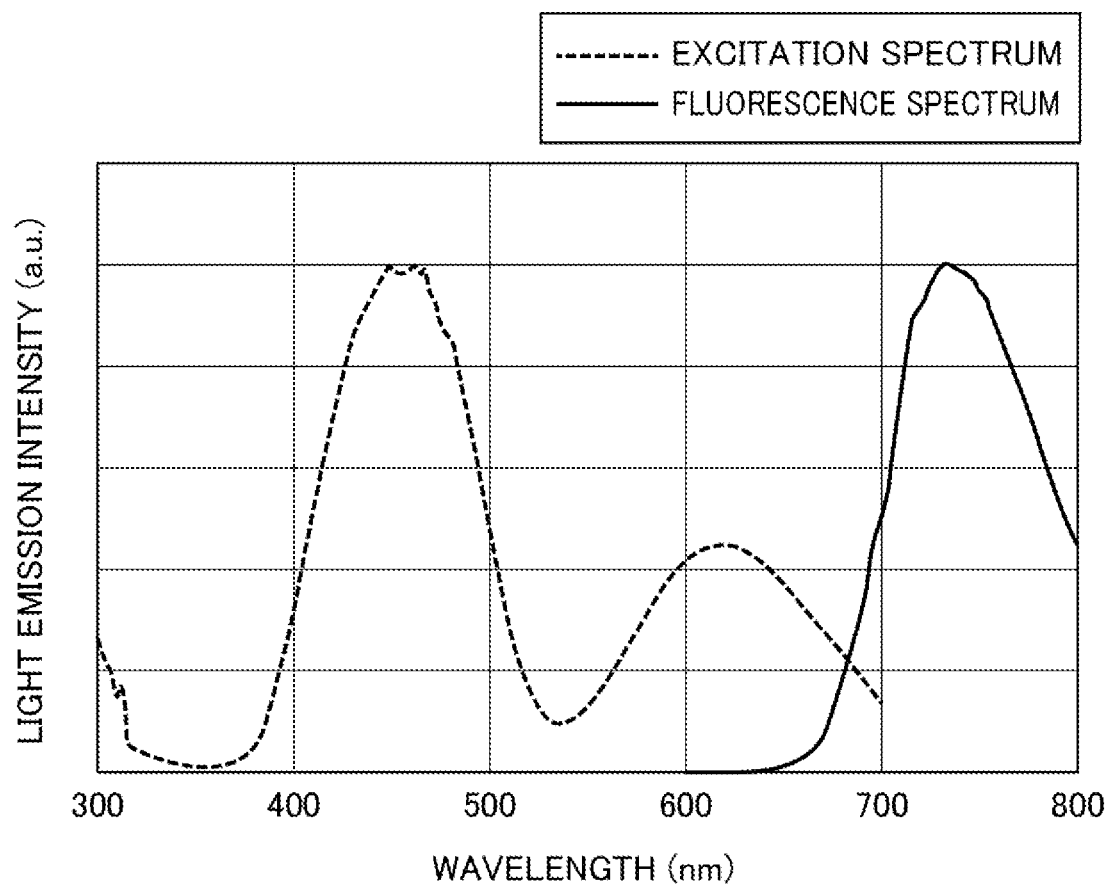
FIG. 2 is an example of an excitation spectrum and a fluorescence spectrum of a first phosphor.

FIG. 2 is an example of an excitation spectrum and a fluorescence spectrum of the first phosphor 2. For example, as illustrated in FIG. 2, the first phosphor 2 strongly absorbs a light in a blue wavelength range of 400 nm or more to less than 500 nm, and a light in an orange to red wavelength range of 580 nm or more to less than 660 nm. The first phosphor 2 absorbs the blue light and the orange-red light, converts the wavelength thereof, and emits a near-infrared fluorescence of 680 nm or more to less than 800 nm.

Figure 3:
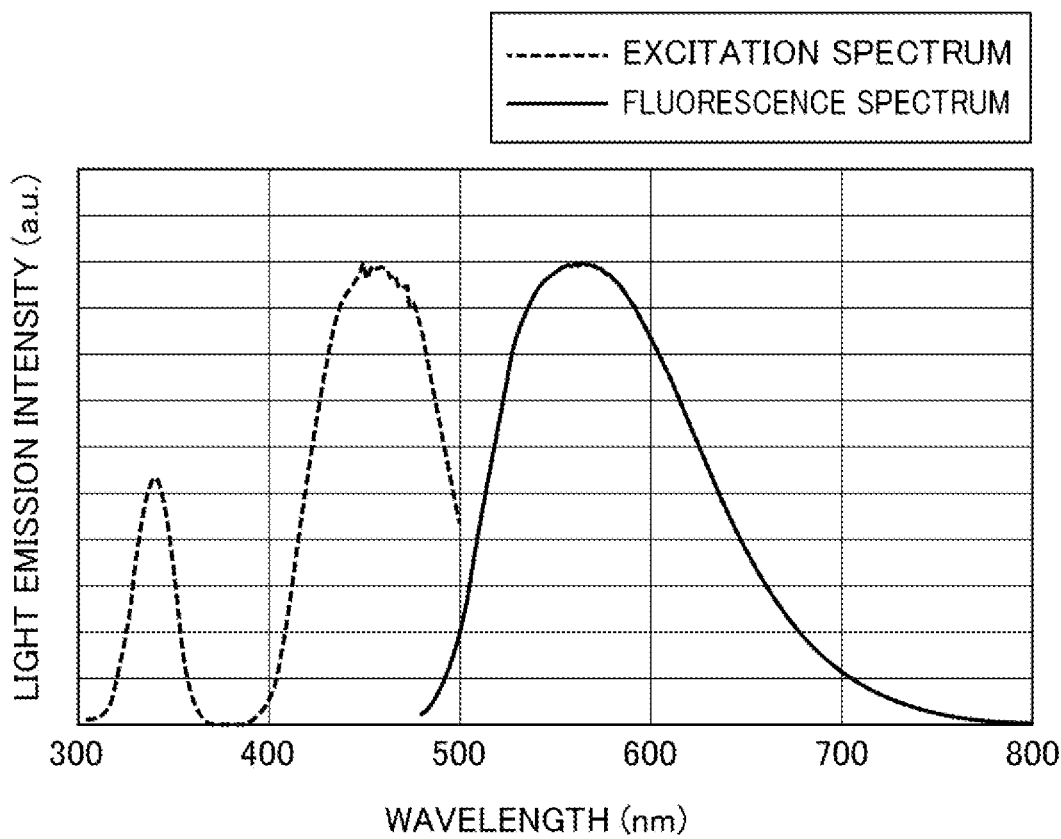
FIG. 3 is an example of an excitation spectrum and a fluorescence spectrum of a second phosphor.

FIG. 3 is an example of an excitation spectrum and a fluorescence spectrum of the second phosphor 3. The fluorescence spectrum of the fluorescence emitted by the second phosphor 3 has a peak where the fluorescence intensity shows a maximum value in a wavelength range of 500 nm or more to less than 580 nm. Specifically, as illustrated in FIG. 3, the fluorescence spectrum of the fluorescence emitted by the second phosphor 3 includes a green to yellow fluorescence component in a wavelength range of 500 nm or more to less than 580 nm as a main fluorescence component and has a broad fluorescence component including a blue fluorescence component and an orange to red fluorescence component.

As described above, the wavelength converter 1 includes the first phosphor 2 and the second phosphor 3. Therefore, the blue and orange to red fluorescent components emitted by the second phosphor 3 are absorbed by the first phosphor 2 and are wavelength-converted into a near-infrared fluorescence.

As a result, the intensity of the blue and orange to red fluorescent components among the broad fluorescent components emitted by the second phosphor 3 decreases, and the intensity of the green to yellow fluorescent component emitted by the second phosphor 3 relatively increases. In particular, the intensity of the deep red fluorescent component among the broad fluorescent components emitted by the second phosphor 3 decreases. In contrast, since the first phosphor 2 emits a near-infrared fluorescence, the intensity of the near-infrared fluorescence component emitted by the wavelength converter 1 increases.

That is, in the light emitted by the wavelength converter 1, the intensity of the green to yellow and near-infrared fluorescent components increases, and the intensity of the orange to red fluorescent component decreases. Therefore, the wavelength converter 1 emits a wavelength-converted light in which the green to yellow fluorescent component and the near-infrared fluorescent component are sufficiently separated. The wavelength converter 1 emits a wavelength-converted light in which the intensity of the deep red fluorescent component, which becomes noise in a near-infrared image sensor, is relatively small.

The green to yellow fluorescent component emitted by the wavelength converter 1 is usable as a light component advantageous for the visual inspection of a diseased part of a patient. The near-infrared fluorescent component emitted by the wavelength converter 1 is usable as a light component advantageous for excitation of a fluorescent drug administered in a living body. The wavelength converter 1 is thus suitable for the coexistence of normal observation using visible light and special observation using near-infrared light.

The wavelength converter 1 emits a fluorescence having a light component over the entire wavelength range of 500 nm or more to less than 580 nm. Emitting such a fluorescence enables the wavelength converter 1 to effectively emit a green to yellow fluorescent component that is advantageous for visual inspection of a diseased part of a patient. The fluorescence emitted by the wavelength converter 1 may have a light component over the entire wavelength range of 500 nm or more to less than 600 nm.

The wavelength converter 1 emits a light having a spectrum in which the ratio of the minimum light emission intensity to the maximum light emission intensity is 40% or less within a wavelength range of 550 nm or more to 700 nm or less. The ratio of the minimum light emission intensity to the maximum light emission intensity is preferably 30% or less, more preferably 20% or less, still more preferably 10% or less, particularly preferably 5% or less. This enables the wavelength converter 1 to emit a wavelength-converted light in which the green to yellow fluorescent component and the near-infrared fluorescent component are more separated. A wavelength having the maximum light emission intensity may be 550 nm or more and less than 580 nm. A wavelength having the minimum light emission intensity may be 580 nm or more and 700 nm or less, 600 nm or more and 700 nm or less.

The fluorescence emitted by the first phosphor 2 preferably has a light component over the entire wavelength range of 700 nm or more to 800 nm or less, more preferably has a light component over the entire wavelength range of 750 nm or more to 800 nm or less. This enables the wavelength converter 1 to emit a near-infrared excitation light capable of efficiently exciting a drug, even if a drug having a light absorption property of near-infrared rays that is likely to vary is used. Thus, a light emitting device 10 having a large number of near-infrared lights emitted by a fluorescent drug or heat rays emitted by a photosensitive drug is obtained.

Preferably, the fluorescence spectrum of the fluorescence emitted by the first phosphor 2 has a peak where the fluorescence intensity shows a maximum value in a wavelength range of 710 nm or more. This enables the wavelength converter 1 to emit a fluorescence including a large number of near-infrared light components with high living body permeability. The fluorescence spectrum of the fluorescence emitted by the first phosphor 2 may have a peak where the fluorescence intensity shows a maximum value in a wavelength range of 710 nm or more to 900 nm or less.

Preferably, the fluorescence emitted by the first phosphor 2 includes a fluorescence based on the electronic energy transition of $Cr^{3+}$, and the fluorescence spectrum of the fluorescence emitted by the first phosphor 2 has a peak where the fluorescence intensity shows a maximum value in a wavelength range exceeding 720 nm. This enables the first phosphor 2 to emit a fluorescence in which a broad spectral component of a short afterglow property is more dominant than a linear spectral component of a long afterglow property. As a result, the wavelength converter 1 emits a light including a large number of near-infrared components. The linear spectrum component is a fluorescence component based on the electron energy transition (spin-forbidden transition) of $^2E \rightarrow {}^4A_2(t_2{}^3)$ of $Cr^{3+}$ and has a peak where the fluorescence intensity shows a maximum value in a wavelength range of 680 nm to 720 nm. The broad spectral component is a fluorescence component based on the electron energy transition (spin-allowed transition) of $^4T_2(t_2{}^2e) \rightarrow {}^4A_2(t_2{}^3)$ of $Cr^{3+}$ and has a peak where the fluorescence intensity shows a maximum value in a wavelength range exceeding 720 nm.

The fluorescence spectrum of the fluorescence emitted by the first phosphor 2 more preferably has a peak where the fluorescence intensity shows a maximum value in a wavelength range exceeding 730 nm, still more preferably has a peak where the fluorescence intensity shows a maximum value in a wavelength range exceeding 750 nm.

The $1/10$ afterglow time of the fluorescence emitted by the first phosphor 2 is preferably less than 1 ms, more preferably less than 300 μs, still more preferably less than 100 μs. Thus, even when the light density of the excitation light for exciting the first phosphor 2 is high, the output of the fluorescence emitted by the first phosphor 2 hardly saturates. Thus, the wavelength converter 1 capable of emitting a high output near-infrared light is obtained. Note that the $1/10$ afterglow time means time $\tau_{1/10}$ taken from the time when the maximum light emission intensity is shown to the time when the intensity becomes $1/10$ of the maximum light emission intensity.

Preferably, the $1/10$ afterglow time of the fluorescence emitted by the first phosphor 2 is longer than the $1/10$ afterglow time of the fluorescence emitted by the second phosphor 3. Preferably, the $1/10$ afterglow time of the fluorescence emitted by the first phosphor 2 is specifically 10 μs or more. Note that the $1/10$ afterglow time of the fluorescence emitted by the first phosphor 2 activated with $Cr^{3+}$ is longer than the $1/10$ afterglow time of a short afterglow (less than 10 μs) fluorescence based on a parity-allowed transition of $Ce^{3+}$, $Eu^{2+}$, or the like. This is because the fluorescence emitted by the first phosphor 2 is a fluorescence based on the electron energy transition of the spin-allowed type of $Cr^{3+}$, which has relatively long afterglow time.

Preferably, the $1/10$ afterglow time difference, which is the difference between the $1/10$ afterglow time of the fluorescence emitted by the first phosphor 2 and the $1/10$ afterglow time of the fluorescence emitted by the second phosphor 3, exceeds 50 μs. Thus, even if the intensity of the fluorescent component of the visible light emitted by the second phosphor 3 as the main component is greatly reduced, the fluorescent component of the near infrared light emitted by the first phosphor 2 as the main component maintains a relatively large intensity. It is thus possible to control the output ratio of the near-infrared fluorescent component and the visible fluorescent component by using the afterglow time difference. Preferably, the $1/10$ afterglow time difference is less than 1 ms.

Preferably, in the fluorescence spectrum of the fluorescence emitted by the first phosphor 2, the spectral width at an intensity of 80% of the maximum value of the fluorescence intensity is 20 nm or more and less than 80 nm. Thus, the main component of the fluorescence emitted by the first phosphor 2 becomes a broad spectrum component. Therefore, even when there is a variation in the wavelength dependence of the sensitivity of a fluorescent drug or photosensitive drug in a medical field using a fluorescence imaging method or photodynamic therapy (PDT method), the wavelength converter 1 emits high output near-infrared light that enables these drugs to function sufficiently.

Preferably, in the fluorescence spectrum of the fluorescence emitted by the first phosphor 2, the ratio of the fluorescence intensity at a wavelength of 780 nm to the maximum fluorescence intensity exceeds 30%. The ratio of the fluorescence intensity at a wavelength of 780 nm to the maximum fluorescence intensity more preferably exceeds 60%, even more preferably exceeds 80%. This enables the first phosphor 2 to emit a fluorescence including a large number of fluorescent components of a near-infrared wavelength range (650 to 1000 nm) through which light easily penetrates the living body, which is called a "living body window". Therefore, the above-described wavelength converter 1 increases the light intensity of the near infrared that penetrates the living body.

Preferably, the fluorescence spectrum of the fluorescence emitted by the first phosphor 2 does not leave a trail of a linear spectral component derived from the electronic energy transition of $Cr^{3+}$. That is, preferably, the fluorescence emitted by the first phosphor 2 has only a broad spectral component (short afterglow property) having a peak where the fluorescence intensity shows a maximum value in a wavelength range exceeding 720 nm. Thus, the first phosphor 2 does not include a long afterglow fluorescent component due to the spin-forbidden transition of $Cr^{3+}$ but only includes a short afterglow fluorescent component due to the spin-allowed transition of $Cr^{3+}$. Thus, even when the light density of the excitation light for exciting the first phosphor 2 is high, the output of the fluorescence emitted by the first phosphor 2 hardly saturates. Therefore, the light emitting device of a point light source capable of emitting a near-infrared light of higher output is obtained.

Preferably, the first phosphor 2 includes no activator other than $Cr^{3+}$. This enables the light absorbed by the first phosphor 2 to be converted into only the fluorescence based on the electronic energy transition of $Cr^{3+}$, which provides the wavelength converter 1 with easy design of output light for maximizing the output ratio of the near-infrared fluorescent component.

Preferably, the first phosphor 2 includes two or more kinds of $Cr^{3+}$-activated phosphors. This enables the output light component in at least the near-infrared wavelength range to be controlled, which provides the wavelength converter 1 with easy adjustment of the spectral distribution in accordance with the application utilizing the near-infrared fluorescence component.

The first phosphor 2 is preferably an oxide-based phosphor, more preferably an oxide phosphor. The oxide-based phosphor means a phosphor including oxygen but not nitrogen or sulfur. The oxide-based phosphor may include at least one selected from the group consisting of an oxide, a complex oxide, and a compound including oxygen or halogen as an anion.

Since the oxide is stable in the atmosphere, even when the oxide phosphor generates heat due to high density photoexcitation by laser light, it is difficult for phosphor crystals to be altered by oxidation in the atmosphere, as occurs in nitride phosphors. Therefore, when all the phosphors in the wavelength converter 1 are oxide phosphors, the light emitting device that is highly reliable is obtained.

Preferably, the first phosphor 2 has a garnet crystal structure. Preferably, the first phosphor 2 is an oxide phosphor with a garnet crystal structure. Since a garnet phosphor is easily deformed in composition and provides a number of phosphor compounds, a crystal field around $Cr^{3+}$ is easily adjusted, and the color tone of fluorescence based on the electronic energy transition of $Cr^{3+}$ is easily controlled.

The phosphor with a garnet structure, especially the oxide, has a polyhedral particle shape close to a sphere and has excellent dispersibility of a phosphor particle group. Therefore, when the phosphor included in the wavelength converter 1 has a garnet structure, the wavelength converter 1 excellent in light transmittance is manufactured relatively easily, which enables higher output of the light emitting device. Further, since a phosphor with a garnet crystal structure has practical experience as a phosphor for LEDs, the light emitting device that is a highly reliable is obtained when the first phosphor 2 has the garnet crystal structure.

The first phosphor 2 may include at least one phosphor selected from the group consisting of: $Lu_2CaMg_2(SiO_4)_3$:$Cr^{3+}$, $Y_3Ga_2(AlO_4)_3$:$Cr^{3+}$, $Y_3Ga_2(GaO_4)_3$:$Cr^{3+}$, $Gd_3Ga_2(AlO_4)_3$:$Cr^{3+}$, $Gd_3Ga_2(GaO_4)_3$:$Cr^{3+}$, $(Y,La)_3Ga_2(GaO_4)_3$:$Cr^{3+}$, $(Gd,La)_3Ga_2(GaO_4)_3$:$Cr^{3+}$, $Ca_2LuZr_2(AlO_4)_3$:$Cr^{3+}$, $Ca_2GdZr_2(AlO_4)_3$:$Cr^{3+}$, $Lu_3Sc_2(GaO_4)_3$:$Cr^{3+}$, $Y_3Sc_2(AlO_4)_3$:$Cr^{3+}$, $Y_3Sc_2(GaO_4)_3$:$Cr^{3+}$, $Gd_3Sc_2(GaO_4)_3$:$Cr^{3+}$, $La_3Sc_2(GaO_4)_3$:$Cr^{3+}$, $Ca_3Sc_2(SiO_4)_3$:$Cr^{3+}$, $Ca_3Sc_2(GeO_4)_3$:$Cr^{3+}$, $BeAl_2O_4$:$Cr^{3+}$, $LiAl_5O_8$:$Cr^{3+}$, $LiGa_5O_8$:$Cr^{3+}$, $Mg_2SiO_4$:$Cr^{3+}$, $Li^+$, $La_3Ga_5GeO_{14}$:$Cr^{3+}$, and $La_3Ga_{5.5}Nb_{0.5}O_{14}$:$Cr^{3+}$.

As described above, the fluorescence emitted by the first phosphor 2 has a specific fluorescence component based on the electronic energy transition of $Cr^{3+}$. This enables the wavelength converter 1 to efficiently excite a fluorescent drug, such as ICG, or a photosensitive drug (which is also a fluorescent drug), such as phthalocyanine.

The second phosphor 3 is a phosphor activated with at least one ion of $Ce^{3+}$ or $Eu^{2+}$. Preferably, the second phosphor 3 is a phosphor activated with $Ce^{3+}$. The phosphor activated with $Ce^{3+}$ has a phtophysical property of emitting fluorescence having a spectral shape with a long tail at a long wavelength side. Thus, the light emitted by the second phosphor 3 has a large proportion of an orange to red fluorescent component, which is advantageous for the excitation of the first phosphor 2, and thus is advantageous for enhancing the intensity of the near-infrared fluorescent component emitted by the first phosphor 2.

The second phosphor 3 may be at least one of an oxide-based phosphor, such as an oxide or a halogen oxide, or a nitride-based phosphor, such as a nitride or an oxynitride.

Preferably, the second phosphor 3 is a $Ce^{3+}$-activated phosphor having a matrix of a compound with at least one, as a main component, selected from the compound group consisting of a garnet type crystal structure, a calcium ferrite type crystal structure, and a lanthanum silicon nitride ($La_3Si_6N_{11}$) type crystal structure. Preferably, the second phosphor 3 is a $Ce^{3+}$-activated phosphor having a matrix of at least one selected from the compound group consisting of a garnet type crystal structure, a calcium ferrite type crystal structure, and a lanthanum silicon nitride ($La_3Si_6N_{11}$) type crystal structure. Using the above-described second phosphor 3 provides output light with a large number of light components from green to yellow.

Preferably, the second phosphor 3 is specifically a $Ce^{3+}$-activated phosphor having a matrix of a compound with at least one, as a main component, selected from the group consisting of $M_3RE_2(SiO_4)_3$, $RE_3Al_2(AlO_4)_3$, $MRE_2O_4$, and $RE_3Si_6N_{11}$. Preferably, the second phosphor 3 is a $Ce^{3+}$-activated phosphor having a matrix of at least one selected from the group consisting of $M_3RE_2(SiO_4)_3$, $RE_3Al_2(AlO_4)_3$, $MRE_2O_4$, and $RE_3Si_6N_{11}$. Preferably, the second phosphor 3 is a $Ce^{3+}$-activated phosphor having a matrix of a solid solution having the above-described compound as an end component. Note that M is an alkaline earth metal, and RE is a rare earth element.

The above-described second phosphor 3 well absorbs light in a wavelength range of 430 nm or more to 480 nm or less and converts it to green to yellow light with a peak where the fluorescence intensity shows a maximum value in a wavelength range of 540 nm or more to less than 580 nm with high efficiency. Therefore, a visible light component is easily obtained by using such a phosphor as the second phosphor 3 with the light source 5 that emits cold color light in a wavelength range of 430 nm or more to 480 nm or less as the primary light 6.

Preferably, the wavelength converter 1 includes an inorganic material. Here, the inorganic material means materials other than organic materials and includes ceramics and metals as a concept. When the wavelength converter 1 includes an inorganic material, the wavelength converter 1 has the heat conductivity higher than that of the wavelength converter including an organic material, such as a sealing resin, thereby facilitating the heat radiation design. Thus, the temperature rise of the wavelength converter 1 is effectively prevented even when the phosphor is photoexcited with high density by the primary light 6 emitted from the light source 5. As a result, the temperature quenching of the phosphor in the wavelength converter 1 is prevented, and thus higher output of light emission is possible. Accordingly, the heat dissipation of the phosphor is improved, and thus the decrease in output of the phosphor due to temperature quenching is prevented, and high output near-infrared light is emitted.

Preferably, all of the wavelength converter 1 is made of an inorganic material. As a result, the heat dissipation of the first phosphor 2 and the second phosphor 3 is improved, and thus the decrease in output of the phosphor due to temperature quenching is prevented, and the light emitting device that emits a high output near-infrared light is obtained.

At least one of the first phosphor 2 or the second phosphor 3 may be a ceramic. This increases the thermal conductivity of the wavelength converter 1, which provides the light emitting device 10 with less heat generation and high output. Here, the ceramic means a sintered body in which particles are bonded to each other.

As illustrated in FIG. 1, preferably, the wavelength converter 1 further includes a sealing material 4 that disperses the first phosphor 2 and the second phosphor 3, in addition to the first phosphor 2 and the second phosphor 3. Preferably, the wavelength converter 1 has the first phosphor 2 and the second phosphor 3 dispersed in the sealing material 4. By dispersing the first phosphor 2 and the second phosphor 3 in the sealing material 4, the light emitted to the wavelength converter 1 is efficiently absorbed and wavelength-converted into a near-infrared light. Further, the wavelength converter 1 is easily formed into a sheet shape or a film shape.

Preferably, the sealing material 4 is at least one of an organic material or an inorganic material, particularly at least one of a transparent (light transmitting) organic material or a transparent (light transmitting) inorganic material. Examples of the sealing material of the organic material include a transparent organic material, such as a silicone resin. Examples of the sealing material of the inorganic material include a transparent inorganic material, such as a low melting point glass.

As described above, the wavelength converter 1 preferably includes an inorganic material, and thus the sealing material 4 preferably includes an inorganic material. Preferably, zinc oxide (ZnO) is used as the inorganic material. This further enhances the heat dissipation of the phosphor, which prevents the output of the phosphor from decreasing due to temperature quenching and provides the wavelength converter 1 that emits high output near-infrared light.

Figure 4:
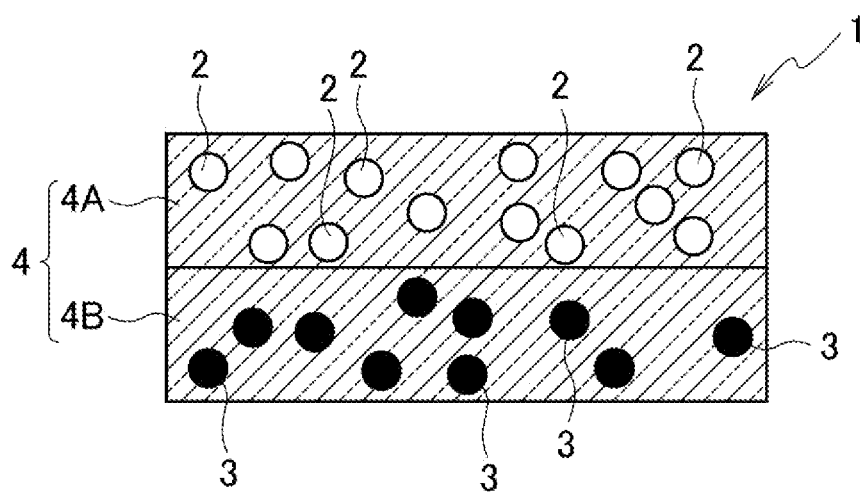
FIG. 4 is a schematic sectional view of another example of the wavelength converter according to the present embodiment.

FIG. 1 illustrates an example in which the first phosphor 2 and the second phosphor 3 are uniformly mixed and dispersed in a single layer of the sealing material 4. However, the wavelength converter 1 is not limited to such a configuration. As illustrated in FIG. 4, for example, the wavelength converter 1 may have a first sealing material 4A and a second sealing material 4B. The first phosphor 2 may be dispersed in the first sealing material 4A, and the second phosphor 3 may be dispersed in the second sealing material 4B. As illustrated in FIG. 4, the first sealing material 4A and the second sealing material 4B each may form a layer, and layers may be stacked to overlap each other. The first sealing material 4A and the second sealing material 4B may be formed of the same material or different materials.

Figure 5:
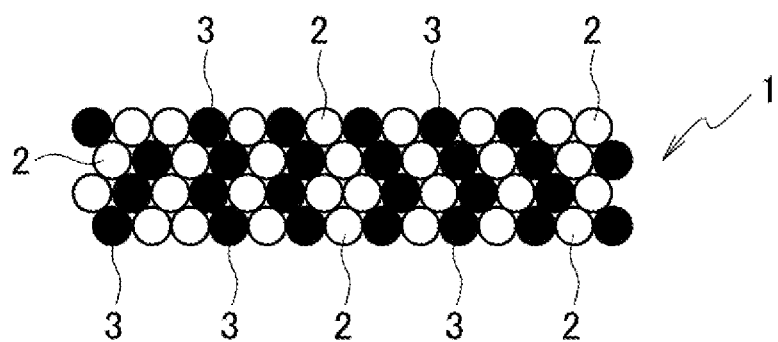
FIG. 5 is a schematic sectional view of another example of the wavelength converter according to the present embodiment.
Figure 6:
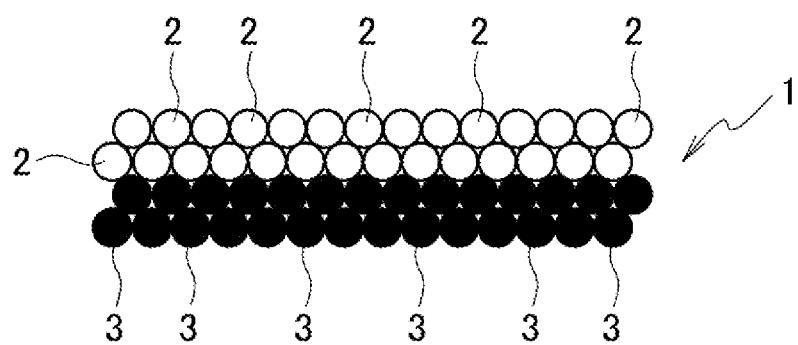
FIG. 6 is a schematic sectional view of another example of the wavelength converter according to the present embodiment.

As illustrated in FIGS. 5 and 6, the wavelength converter 1 may not use the sealing material 4. More specifically, as illustrated in FIG. 5, the wavelength converter 1 does not have the sealing material 4, and the first phosphor 2 and the second phosphor 3 may be uniformly mixed and dispersed. As illustrated in FIG. 6, the wavelength converter 1 does not have the sealing material 4, the first phosphor 2 and the second phosphor 3 may each form an aggregated layer, and layers may be stacked to overlap each other. In this case, the phosphor may be fixed to each other by using an organic or inorganic binder. The phosphor is fixable to each other by using the heating reaction of the phosphor. As the binder, a commonly used resin-based adhesive, ceramic fine particles, low melting point glass, or the like is usable. The wavelength converter 1 without using the sealing material 4 is made thin and thus is suitably used for the light emitting device.

[Light Emitting Device]

Next, the light emitting device 10 according to the present embodiment is described with reference to FIGS. 7 and 8.

Figure 7:
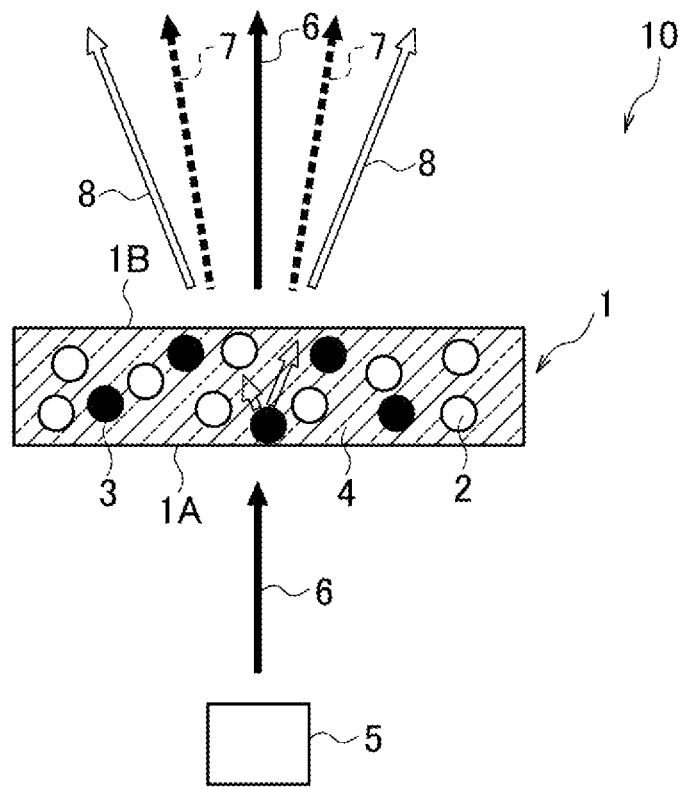
FIG. 7 is a schematic sectional view of an example of a light emitting device according to the present embodiment.
Figure 8:
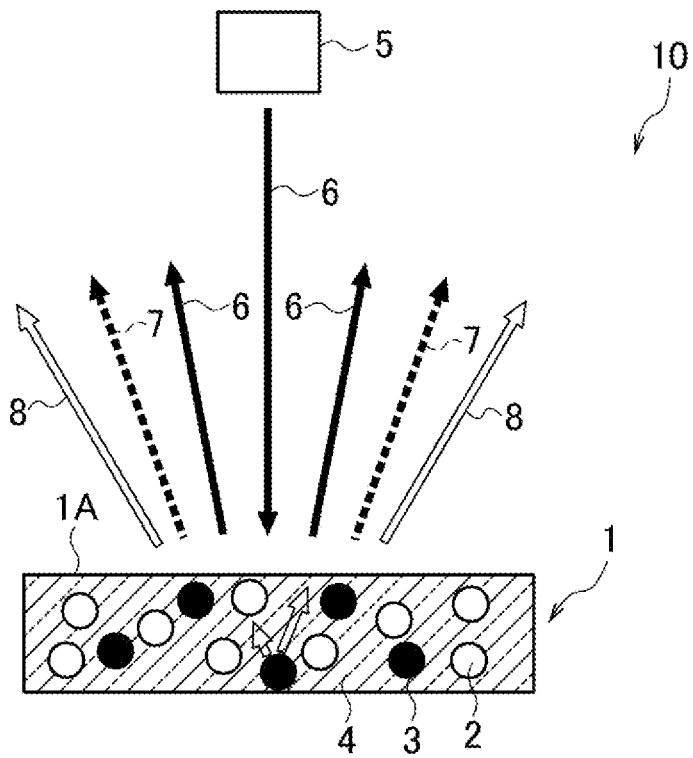
FIG. 8 is a schematic sectional view of another example of the light emitting device according to the present embodiment.

As illustrated in FIG. 7, the light emitting device 10 according to the present embodiment includes the above-described wavelength converter 1 and the light source 5 emitting a light that is wavelength-converted by the wavelength converter 1. That is, the light emitting device 10 is the light emitting device 10 including at least a combination of the light source 5 emitting the primary light 6, the first phosphor 2, and the second phosphor 3. The wavelength converter 1 receives the primary light 6 emitted by the light source 5 and emits a fluorescence having a wavelength longer than that of the primary light 6. The light emitting device 10 in FIG. 7 receives the primary light 6 at the front 1A of the wavelength converter 1 and emits fluorescence from the back 1B of the wavelength converter 1.

The emitted fluorescence includes a first wavelength-converted light 7 and a second wavelength-converted light 8. The second wavelength-converted light 8 is a fluorescence emitted by wavelength conversion of a part of the primary light 6 absorbed by the second phosphor 3. The first wavelength-converted light 7 is a fluorescence emitted by wavelength conversion of a part of the primary light 6 and/or the second wavelength-converted light 8 absorbed by the first phosphor 2. The first wavelength-converted light 7 having a specific fluorescence component based on the electronic energy transition of $Cr^{3+}$ enables the light emitting device 10 to emit a fluorescence based on the electronic energy transition of $Cr^{3+}$.

As described above, the wavelength converter 1 emits a wavelength-converted light in which the green to yellow fluorescent component and the near-infrared fluorescent component are sufficiently separated. Therefore, the above-described light emitting device 10 emits output light in which the green to yellow fluorescent components and the near-infrared fluorescent components are sufficiently separated. The green to yellow fluorescent component is usable as a light component that is advantageous for visual inspection of a diseased area of a patient. In contrast, the near-infrared fluorescent component is usable as a light component advantageous for excitation of a drug administered in a living body. For this reason, the light emitting device 10 is advantageous in diagnosing because it achieves the coexistence of normal observation using visible light and special observation using near-infrared light.

As described above, the light source 5 emits a light that is wavelength-converted by the wavelength converter 1, and the light emitted by the light source 5 is preferably a laser light. The laser light is a high-output point light source with strong directivity, and thus it not only reduces the size of the optical system and the diameter of the light guiding part but also improves the coupling efficiency of the laser light to an optical fiber. Accordingly, the light emitting device 10 that facilitates high output is obtained. Preferably, the laser light is emitted by a semiconductor light emitting device from the viewpoint of miniaturization of the light emitting device 10.

Preferably, the spectrum of the light emitted by the light source 5 has a peak where the intensity shows a maximum value in a range of 400 nm or more to less than 500 nm. Also preferably, the spectrum of the light emitted by the light source 5 has a peak where the intensity shows a maximum value in a wavelength range of 420 nm or more to less than 480 nm, and the light emitted by the light source 5 is blue light. The spectrum of the light emitted by the light source 5 has a peak where the intensity shows a maximum value more preferably in a wavelength range of 430 nm or more to less than 480 nm, even more preferably in a wavelength range of 440 nm or more to less than 470 nm. In this way, not only the first phosphor 2 activated with $Cr^{3+}$ is excited with high efficiency, but also a high-efficiency phosphor having a high performance for LED lighting is usable as the second phosphor 3 activated with at least one of $Ce^{3+}$ or $Eu^{2+}$. Thus, the light emitting device 10 with high output is obtained.

The light source 5 may include a red laser device. The light source 5 may include a blue laser device. The red laser device has a small energy difference from the near-infrared light component and a small energy loss associated with wavelength conversion, which is preferable in achieving high efficiency of the light emitting device 10. In contrast, a laser device with high efficiency and high output is easily available for the blue laser device, and thus the blue laser device is preferable in achieving high output of the light emitting device 10. Preferably, the light source 5 includes a blue laser device as an excitation source and emits blue laser light. Thus, the first phosphor 2 and the second phosphor 3 are excited with high efficiency and high output, which enables the light emitting device 10 to emit high-output near-infrared light.

Preferably, the light source 5 includes a solid-state light emitting device, and the above-described blue light is emitted by the solid-state light emitting device. In this way, a small-sized light emitting device with high reliability is used as a light emitting source of the above-described blue light, which provides a small-sized light emitting device 10 with high reliability.

The solid-state light emitting device is a light emitting device that emits the primary light 6. Any solid-state light emitting device is usable as long as it emits the primary light 6 with a high energy density. The solid-state light emitting device is preferably at least one of a laser device or a light-emitting diode (LED), more preferably a laser device. The light source 5 may be, for example, a surface emitting laser diode.

The rated light output of the solid-state light emitting device is preferably 1 W or more, more preferably 3 W or more. This enables the light source 5 to emit the primary light 6 with high output, and thus the light emitting device 10 that facilitates high output is obtained.

The upper limit of the rated light output is not limited, and the rated light output is increased by the light source 5 having a plurality of solid-state light emitting devices. However, for practical purposes, the rated light output is preferably less than 10 kW, more preferably less than 3 kW.

The light density of the primary light 6 is preferably more than 0.5 W/mm$^2$, more preferably more than 3 W/mm$^2$, still more preferably more than 10 W/mm$^2$. The light density may exceed 30 W/mm$^2$. In this way, the first phosphor 2 and the second phosphor 3 are photoexcited at high density, which enables the wavelength converter 1 to emit a fluorescent component of high output.

Preferably, the primary light 6 is a continuous pulsed light. In this way, immediately after the pulsed light is turned off, the first wavelength-converted light 7 having a near-infrared fluorescent component emits phosphorescence longer than the second wavelength-converted light 8 that becomes visible light. Utilizing the phosphorescence component as the excitation light of the above-described drug provides the light emitting device 10 that is easily designed so that only the near-infrared fluorescent component emitted by the drug enters the image sensor, and the second wavelength-converted light 8 hardly enters the image sensor. Accordingly, the light emitting device 10 advantageous for the improvement of the S/N ratio of the near-infrared fluorescent component emitted by the drug is obtained.

Preferably, the correlated color temperature of the mixed light of the primary light 6 and the second wavelength converter light 8 is 2500 K or more and less than 7000 K. The correlated color temperature is more preferably 2700 K or more and less than 5500 K, more preferably 2800 K or more and less than 3200 K or 4500 K or more and less than 5500 K. The output light with a correlated color temperature within the above-described range is a white output light, and a diseased part visible through an image display device or an optical device appears similar to the diseased part observed under natural light. Therefore, the light emitting device 10 is obtained that easily makes use of the medical experience of doctors, which is preferable for medical use.

Next, the operation of the light emitting device 10 according to the present embodiment is described. In the light emitting device 10 illustrated in FIG. 7, first, the primary light 6 emitted by the light source 5 is emitted to a front 1A of the wavelength converter 1. Most of the emitted primary light 6 enters the wavelength converter 1 from the front 1A of the wavelength converter 1 and passes through the wavelength converter 1, and a part of the emitted primary light 6 is reflected on the surface of the wavelength converter 1. The second phosphor 3 absorbs a part of the primary light 6 and converts it into the second wavelength-converted light 8, and the first phosphor 2 absorbs a part of the primary light 6 and/or a part of the second wavelength-converted light 8 and converts it into the first wavelength-converted light 7. Thus, the light emitting device 10 emits a light including the primary light 6, the first wavelength-converted light 7, and the second wavelength-converted light 8 from a back 1B of the wavelength converter 1, as output light.

The light emitting device 10 is not limited to the configuration in FIG. 7 and is not limited to the configuration of receiving the primary light 6 from the front 1A of the wavelength converter 1 and emitting the first wavelength-converted light 7 and the second wavelength-converted light 8 from the back 1B of the wavelength converter 1 as illustrated in FIG. 7. As illustrated in FIG. 8, the light emitting device 10 may receive the primary light 6 from the front 1A of the wavelength converter 1 and emit the first wavelength-converted light 7 and the second wavelength-converted light 8 from the front 1A of the wavelength converter 1. Specifically, in the light emitting device 10 illustrated in FIG. 8, first, the primary light 6 emitted by the light source 5 is emitted to the front 1A of the wavelength converter 1. Most of the emitted primary light 6 enters the wavelength converter 1 from the front 1A of the wavelength converter 1, and a part of the emitted primary light 6 is reflected on the surface of the wavelength converter 1. The second phosphor 3 absorbs a part of the primary light 6 and converts it into the second wavelength-converted light 8, and the first phosphor 2 absorbs a part of the primary light 6 and/or a part of the second wavelength-converted light 8 and converts it into the first wavelength-converted light 7. In this way, the light emitting device 10 emits a light including the primary light 6, the first wavelength-converted light 7, and the second wavelength-converted light 8 from the front 1A of the wavelength converter 1, as output light.

Thus, the light emitting device 10 according to the present embodiment emits the first wavelength-converted light 7 including a large number of long-afterglow near-infrared fluorescent components based on the electron energy transition of $Cr^{3+}$. The near-infrared fluorescent component is usable as a light component advantageous for excitation of the fluorescent drug administered in a living body. The light emitting device 10 according to the present embodiment emits the second wavelength-converted light 8 including a large number of short-afterglow green to yellow fluorescent components based on the electronic energy transition of $Ce^{3+}$ or $Eu^{2+}$. The green to yellow fluorescent component is usable as a light component that is advantageous for visual inspection of a diseased part of a patient.

Accordingly, the light emitting device 10 may be used for medical purposes. That is, the light emitting device 10 may be a medical light emitting device. In other words, the light emitting device 10 may be a medical illumination device. In this way, the light emitting device 10 emits output light in which the green to yellow fluorescent component and the near-infrared fluorescent component are sufficiently separated and thus achieves the coexistence of the normal observation and the special observation as described above, which is advantageous in diagnosing disease state.

The light emitting device 10 may be used for optical coherence tomography (OCT) or the like. However, preferably, the light emitting device 10 is used for either a fluorescence imaging method or photodynamic therapy. The light emitting device 10 used in these methods is a light emitting device for a medical system using a drug, such as a fluorescent drug or a photosensitive drug. These methods are a promising medical technology with a wide range of applications and are highly practical. The light emitting device 10 illuminates the inside of the living body with a broad near-infrared high-output light through the "living body window" and makes the fluorescent drug or photosensitive drug taken into the living body fully functional, which is expected to have a large therapeutic effect.

The fluorescence imaging method is a method of observing a lesion by administering a fluorescent drug that selectively binds to the lesion, such as a tumor, to a subject, exciting the fluorescent drug with a specific light, and detecting and imaging fluorescence emitted from the fluorescent drug with an image sensor. The fluorescence imaging method makes it possible to observe lesions that are difficult to observe using only general illumination. As the fluorescent drug, a drug that absorbs excitation light in the near-infrared range, and emits fluorescence in the near-infrared range and at a wavelength longer than the excitation light is usable. Examples of the fluorescent drug used include at least one selected from the group consisting of indocyanine green (ICG), a phthalocyanine-based compound, a talaporfin sodium-based compound, and a dipicolylcyanine (DIPCY)-based compound.

The photodynamic therapy is a treatment method of administering a photosensitive drug that selectively binds to a target biological tissue to a subject and irradiating the photosensitive drug with near-infrared light. When the photosensitive drug is irradiated with the near-infrared light, the photosensitive drug generates active oxygen, which is usable to treat lesions, such as tumors or infections. Examples of the photosensitive drug used include at least one selected from the group consisting of a phthalocyanine-based compound, a talaporfin sodium-based compound, and a porfimer sodium-based compound.

The light emitting device 10 according to the present embodiment may be used as a light source for a sensing system or an illumination system for a sensing system. With the light emitting device 10, an orthodox light receiving element having light receiving sensitivity in the near-infrared wavelength range may be used to configure a high-sensitivity sensing system. This provides a light emitting device that facilitates miniaturization of the sensing system and broadening of the sensing range.

[Healthcare System]

Next, a medical system including the above-described light emitting device 10 is described. Specifically, as an example of the medical system, an endoscope 11 provided with the light emitting device 10 and an endoscope system 100 using the endoscope 11 are described with reference to FIGS. 9 to 11.

(Endoscope)

As illustrated in FIG. 9, the endoscope 11 according to the present embodiment includes the above-described light emitting device 10. The endoscope 11 includes a scope 110, a light source connector 111, a mount adapter 112, a relay lens 113, a camera head 114, and an operation switch 115.

The scope 110 is an elongated light guide member capable of guiding light from end to end and is inserted into the body when in use. The scope 110 includes an imaging window 110z at its tip. For the imaging window 110z, an optical material, such as optical glass or optical plastic, is used. The scope 110 includes an optical fiber for guiding light introduced from the light source connector 111 to the tip, and an optical fiber for transmitting an optical image that enters through the imaging window 110z.

The light source connector 111 introduces illumination light emitted to a diseased part and the like in the body from the light emitting device 10. In the present embodiment, the illumination light includes visible light and near-infrared light. The light introduced into the light source connector 111 is guided to the tip of the scope 110 through the optical fiber to be emitted to a diseased part and the like in the body from the imaging window 110z. As illustrated in FIG. 9, the light source connector 111 is provided with a transmission cable 111z for guiding illumination light from the light emitting device 10 to the scope 110. The transmission cable 111z may include an optical fiber.

The mount adapter 112 is a member for mounting the scope 110 on the camera head 114. Various scopes 110 are detachably mountable on the mount adapter 112.

The relay lens 113 converges the optical image transmitted through the scope 110 on the imaging surface of the image sensor. The relay lens 113 may be moved in accordance with the operation amount of the operation switch 115 to perform focus adjustment and magnification adjustment.

The camera head 114 includes a color separation prism inside. The color separation prism separates the light converged by the relay lens 113 into four colors of R light (red light), G light (green light), B light (blue light), and IR light (near-infrared light). The color separation prism includes, for example, a light transmitting member, such as glass.

The camera head 114 further includes an image sensor 114A as a detector inside. The image sensor 114A is not limited, but at least one of CCD (Charge Coupled Device) or CMOS (Complementary Metal Oxide Semiconductor) is usable. The image sensor 114A may include multiple types of image sensors.

The image sensor 114A may include, for example, an IR light image sensor 114IR and a visible light image sensor 114V as in FIG. 10. The visible light image sensor 114V may include an R light image sensor 114R, a G light image sensor 114G, and a B light image sensor 114B. The IR light image sensor 114IR is a dedicated sensor for receiving an IR component (near-infrared component) light. The R light image sensor 114R is a dedicated sensor for receiving R component (red component) light. The G light image sensor 114G is a dedicated sensor for receiving G component (green component) light. The B light image sensor 114B is a dedicated sensor for receiving B component (blue component) light. The IR light image sensor 114IR, the R light image sensor 114R, the G light image sensor 114G, and the B light image sensor 114B convert optical images formed on respective imaging surfaces into electric signals.

The camera head 114 may have a color filter inside instead of the color separation prism. The color filter is provided on the imaging surface of the image sensor 114A. For example, four color filters are provided, and the four color filters receive the light converged by the relay lens 113 and selectively transmit R light (red light), G light (green light), B light (blue light), and IR light (near-infrared light), respectively.

Preferably, the color filter for selectively transmitting IR light includes a barrier film for cutting the reflection component of near-infrared light (IR light) included in the illumination light. This enables only the fluorescence composed of IR light emitted from a fluorescent drug, such as ICG, to form an image on the imaging surface of the image sensor 114IR for IR light. Therefore, the diseased part luminous with the fluorescent drug is easily observed clearly.

As illustrated in FIG. 9, a signal cable 114z is connected to the camera head 114 to transmit an electric signal from the image sensor 114A to a CCU 12 described later.

In the endoscope 11 having such a configuration, light from a subject is guided to the relay lens 113 through the scope 110 and is further transmitted through the color separation prism in the camera head 114 to form images on the four image sensors.

(Endoscope System)

As illustrated in FIG. 11, the endoscope system 100 includes the endoscope 11 for imaging the inside of a subject, a CCU (Camera Control Unit) 12, and a display device 13, such as a display.

The CCU 12 includes at least an RGB signal processing unit, an IR signal processing unit, and an output unit. The CCU 12 executes a program stored in the internal or external memory of the CCU 12 to realize the respective functions of the RGB signal processing unit, the IR signal processing unit, and the output unit.

The RGB signal processing unit converts the R component, G component, and B component electrical signals from the visible light image sensor 114V into video signals that are displayable on the display device 13 and outputs the video signals to the output unit. The IR signal processing unit converts the IR component electrical signal from the IR light image sensor 114IR into a video signal and outputs the video signal to the output unit.

The output unit outputs at least one of the video signals of respective RGB color components or the video signal of the IR component to the display device 13. For example, the output unit outputs video signals on the basis of either a simultaneous output mode or a superimposed output mode.

In the simultaneous output mode, the output unit simultaneously outputs the RGB image and the IR image on separate screens. The simultaneous output mode enables the diseased part to be observed by comparing the RGB image and the IR image on the separate screens. In the superimposed output mode, the output unit outputs a composite image in which the RGB image and the IR image are superimposed. The superimposed output mode enables the diseased part luminous with the ICG to be clearly observed, for example in the RGB image.

The display device 13 displays an image of an object, such as a diseased part, on a screen on the basis of video signals from the CCU 12. In the simultaneous output mode, the display device 13 divides the screen into multiple screens and displays the RGB image and the IR image side by side on each screen. In the superimposed output mode, the display device 13 displays a composite image in which an RGB image and an IR image are superimposed on each other on a single screen.

Next, functions of the endoscope 11 and the endoscope system 100 according to the present embodiment are described. When a subject is observed using the endoscope system 100, first, indocyanine green (ICG) as a fluorescent substance is administered to the subject. As a result, ICG accumulates at a site of lymph, tumor, or the like (diseased part).

Next, visible light and near-infrared light are introduced from the light emitting device 10 to the light source connector 111 through the transmission cable 111z. The light introduced into the light source connector 111 is guided to the tip side of the scope 110 and projected from the imaging window 110z to be emitted to the diseased part and the periphery of the diseased part. The light reflected from the diseased part and the like and the fluorescence emitted from the ICG are guided to the rear end side of the scope 110 through the imaging window 110z and the optical fiber, converged by the relay lens 113 to enter into the color separation prism inside the camera head 114.

In the color separation prism, among the incident light, the light of the IR component separated by the IR separation prism is imaged as an optical image of an infrared component by the IR light image sensor 114IR. The light of the R component separated by the red separation prism is imaged as an optical image of the red component by the R light image sensor 114R. The light of the G component separated by the green separation prism is imaged as an optical image of the green component by the G light image sensor 114G. The light of the B component separated by the blue separation prism is imaged as an optical image of the blue component by the B light image sensor 114B.

The electrical signal of the IR component converted by the IR light image sensor 114IR is converted into a video signal by the IR signal processing unit in the CCU 12. The electric signals of the R component, G component, and B component converted by the visible light image sensor 114V are converted into respective video signals by the RGB signal processing unit in the CCU 12. The image signal of the IR component, and the image signals of the R component, G component, and B component in synchronization with each other are output to the display device 13.

When the simultaneous output mode is set in the CCU 12, the RGB image and the IR image are simultaneously displayed on two screens on the display device 13. When the superimposed output mode is set in the CCU 12, a composite image in which the RGB image and the IR image are superimposed is displayed on the display device 13.

As described above, the endoscope 11 according to the present embodiment includes the light emitting device 10. Therefore, by efficiently exciting the fluorescent drug to emit light using the endoscope 11, the diseased part is clearly observed.

Preferably, the endoscope 11 according to the present embodiment further includes a detector for detecting fluorescence emitted from a fluorescent drug that has absorbed the first wavelength-converted light 7. Specifically, preferably, the endoscope 11 includes the image sensor 114A as described above. By providing the endoscope 11 with the detector for detecting fluorescence emitted from a fluorescent drug in addition to the light emitting device 10, the diseased part is specified only by the endoscope 11. This makes it possible to perform medical examination and treatment with less burden on the patient, since there is no need to open the abdomen wide to identify the diseased part as in the conventional method. This also enables the doctor using the endoscope 11 to accurately identify the diseased part, which improves the efficiency of treatment.

Preferably, the medical system is used for either the fluorescence imaging method or photodynamic therapy. The medical system used in these methods is a promising medical technology with a wide range of applications and is highly practical. The medical system illuminates the inside of the living body with a broad near-infrared high-output light through the "living body window" and makes the fluorescent drug or photosensitive drug taken into the living body fully functional, which is expected to have a large therapeutic effect. Further, such a medical system uses the light emitting device 10 having a relatively simple configuration, which is advantageous in reducing the size and the cost.

The medical system may further include a first image sensor and a second image sensor in addition to the light emitting device 10. The first image sensor may detect a reflected light of a visible light component emitted by the light emitting device 10. The second image sensor may detect a near-infrared fluorescence component emitted by the drug. The drug is excited by a light emitted by the light emitting device 10. The first image sensor is, for example, the visible light image sensor 114V as described above. The second image sensor is, for example, the IR light image sensor 114IR as described above. The drug is, for example, the fluorescent drug described above.

In this way, it becomes easy to divide the visual image of a diseased part of a living body and the state observation of a near-infrared fluorescent component emitted by the drug (fluorescent protein) administered into the living body into the first image sensor and the second image sensor, respectively. Such a medical system achieves the coexistence of normal observation and special observation, which is advantageous in diagnosing disease state.

[Electronic Apparatus]

Next, an electronic apparatus according to the present embodiment is described. The electronic apparatus according to the present embodiment includes a light emitting device 10. As described above, the light emitting device 10 is expected to have a large therapeutic effect, and it is easy to miniaturize the sensing system. Since the electronic apparatus according to the present embodiment uses the light emitting device 10, when it is used for a medical device or a sensing device, a large therapeutic effect, miniaturization of the sensing system, and the like are expected.

The electronic apparatus includes, for example, the light emitting device 10, and a light receiving element. The light receiving element is, for example, a sensor, such as an infrared sensor for detecting light in a near-infrared wavelength range. The electronic apparatus may be any of an information recognition device, a sorting device, a detection device, or an inspection device. As described above, these devices also facilitate miniaturization of the sensing system and broadening of the sensing range.

The information recognition device is, for example, a driver support system that recognizes the surrounding situation by detecting reflected components of emitted infrared rays.

The sorting device is, for example, a device that sorts an irradiated object into predetermined categories by using the difference in infrared light components between the irradiation light and reflected light reflected by the irradiated object.

The detection device is, for example, a device that detects a liquid. Examples of liquids include water, and flammable liquids that are prohibited from being transported in aircraft. Specifically, the detection device may be a device for detecting moisture adhering to glass, and moisture absorbed by an object, such as sponge or fine powder. The detection device may visualize the detected liquid. Specifically, the detection device may visualize the distribution information of the detected liquid.

The inspection device may be any of a medical inspection device, an agricultural and livestock inspection device, a fishery inspection device, or an industrial inspection device. These devices are useful for inspecting an inspection object in each industry.

The medical inspection device is, for example, an examination device that examines the health condition of a human or non-human animal. Non-human animals are, for example, domestic animals. The medical inspection device is, for example, a device used for a biological examination, such as a fundus examination or a blood oxygen saturation examination, and a device used for examination of an organ, such as a blood vessel or an organ. The medical inspection device may be a device for examining the inside of a living body or a device for examining the outside of a living body.

The agricultural and livestock inspection device is, for example, a device for inspecting agricultural and livestock products including agricultural products and livestock products. Agricultural products may be used as foods, for example, fruits and vegetables, or cereals, or as fuels, such as oils. Livestock products include, for example, meat and dairy products. The agricultural and livestock inspection device may be a device for non-destructively inspecting the inside or outside of the agricultural and livestock products. Examples of the agricultural and livestock inspection device includes a device for inspecting the sugar content of vegetables and fruits, a device for inspecting the acidity of vegetables and fruits, a device for inspecting the freshness of vegetables and fruits by the visualization of leaf veins, a device for inspecting the quality of vegetables and fruits by the visualization of wounds and internal defects, a device for inspecting the quality of meat, and a device for inspecting the quality of processed foods processed with milk, meat, or the like as raw materials.

The fishery inspection device is, for example, a device for inspecting the flesh quality of fish, such as tuna, or a device for inspecting the presence or absence of the contents in shells of shellfish.

The industrial inspection device is, for example, a foreign matter inspection device, a content inspection device, a condition inspection device, or a structure inspection device.

Examples of the foreign matter inspection device include a device for inspecting foreign matter in a liquid contained in a container, such as a beverage or a liquid medicine, a device for inspecting foreign matter in a packaging material, a device for inspecting foreign matter in a printed image, a device for inspecting foreign matter in a semiconductor or an electronic component, a device for inspecting foreign matter, such as residual bone in food, dust, or machine oil, a device for inspecting foreign matter in processed food in a container, and a device for inspecting foreign matter in medical devices, such as adhesive plasters, medical and pharmaceutical products, or quasi-drugs.

Examples of the content inspection device include a device for inspecting the content of a liquid contained in a container, such as a beverage or a liquid medicine, a device for inspecting the content of a processed food contained in a container, and a device for inspecting the content of asbestos in building materials.

Examples of the state inspection device include a device for inspecting packaging state of a packaging material, and a device for inspecting printing state of a packaging material.

Examples of the structure inspection device include an internal non-destructive inspection device and an external non-destructive inspection device for a composite member or a composite component, such as a resin product. A specific example of the resin product is, for example, a metal brush with a part of metal wire embedded in the resin, and the inspection device inspects the bonding state of the resin and the metal.

The electronic apparatus may use color night vision technology. Color night vision technology uses a correlation of reflection intensity between visible light and infrared rays to colorize an image by assigning infrared rays to RGB signals for each wavelength. According to the color night vision technology, a color image is obtained only by infrared rays, and it is particularly suitable for a security device.

As described above, the electronic apparatus includes the light emitting device 10. When the light emitting device 10 includes a power source, a light source 5, and a wavelength converter 1, it is not necessary to accommodate all of them in one housing. Therefore, the electronic apparatus according to the present embodiment provides a highly accurate and compact inspection method, or the like, with excellent operability.

[Inspection Method]

Next, an inspection method according to the present embodiment is described. As described above, the electronic apparatus including the light emitting device 10 is also usable as an inspection device. That is, the light emitting device 10 is usabel in the inspection method according to the present embodiment. This provides a highly accurate and compact inspection method with excellent operability.

EXAMPLES

The present embodiment is described below in more detail with reference to examples, but the present embodiment is not limited to these examples.

[Preparation of Phosphor]

Example 1

A phosphor activated with $Cr^{3+}$ and a phosphor activated with $Ce^{3+}$ used in example 1 were synthesized using a preparation method utilizing a solid phase reaction. The $Cr^{3+}$-activated phosphor used in example 1 is an oxide phosphor represented by a formula: $Y_3(Ga_{0.97}Cr_{0.03})_2Ga_3O_{12}$. In synthesizing the phosphor activated with $Cr^{3+}$ used in example 1, the following compound powders were used as main raw materials.

Yttrium oxide ($Y_2O_3$): purity 3N, Shin-Etsu Chemical Co., Ltd.

Gallium oxide ($Ga_2O_3$): purity 4N, Wako Pure Chemical Corporation

Chromium oxide ($Cr_2O_3$): Purity 3N, Kojundo Chemical Laboratory Co., Ltd.

First, the above-described raw materials were weighed to obtain a compound of a stoichiometric composition $Y_3(Ga_{0.97}Cr_{0.03})_2Ga_3O_{12}$. The weighed raw materials were then put into a beaker containing pure water and stirred with a magnetic stirrer for 1 hour. Thus, a slurry-like mixed raw material of the pure water and raw materials was obtained. Then, the slurry-like mixed raw material was dried entirely using a dryer. The mixed raw material after drying was pulverized using a mortar and a pestle to obtain a calcined raw material.

The above-described calcined raw material was transferred to a small alumina crucible and calcined in air at 1350° C. to 1450° C. for 1 hour in a box-type electric furnace to obtain the phosphor activated with $Cr^{3+}$. The temperature rise and fall rate was set at 400° C./h. The body color of the obtained phosphor was deep green.

The $Ce^{3+}$-activated phosphor used in example 1 was a commercially available oxide phosphor expressed by a formula: $(Y_{0.75}Gd_{0.22}Ce_{0.03})_3Al_2Al_3O_{12}$.

The obtained phosphor activated with $Cr^{3+}$ and the phosphor activated with $Ce^{3+}$ were mixed so that the weight ratio was 1:1 to obtain a mixed powder of example 1. A mortar and pestle were used for mixing, and the mixing time was 3 minutes.

Example 2

A phosphor activated with $Cr^{3+}$ and a phosphor activated with $Ce^{3+}$ used in example 2 were synthesized using a preparation method utilizing a solid phase reaction. The $Cr^{3+}$-activated phosphor used in example 2 is an oxide phosphor represented by a formula: $(Gd_{0.75}La_{0.25})_3(Ga_{0.97}Cr_{0.03})_2Ga_3O_{12}$. In synthesizing the phosphor activated with $Cr^{3+}$ used in example 2, the following compound powders were used as main raw materials.

Gadolinium oxide ($Gd_2O_3$): purity 3N, Wako Pure Chemical Corporation

Lanthanum oxide ($La_2O_3$): purity 3N, Wako Pure Chemical Corporation

Gallium oxide ($Ga_2O_3$): purity 4N, Wako Pure Chemical Corporation

Chromium oxide ($Cr_2O_3$): Purity 3N, Kojundo Chemical Laboratory Co., Ltd.

First, the above-described raw materials were weighed to obtain a compound of a stoichiometric composition $(Gd_{0.75}La_{0.25})_3(Ga_{0.97}Cr_{0.03})_2Ga_3O_{12}$. The weighed raw materials were then put into a beaker containing pure water and stirred with a magnetic stirrer for 1 hour. Thus, a slurry-like mixed raw material of the pure water and raw materials was obtained. Then, the slurry-like mixed raw material was dried entirely using a dryer. The mixed raw material after drying was pulverized using a mortar and a pestle to obtain a calcined raw material.

The above-described calcined raw material was transferred to a small alumina crucible and calcined in air at 1400° C. to 1500° C. for 1 hour in a box-type electric furnace to obtain the phosphor activated with $Cr^{3+}$. The temperature rise and fall rate was set at 400° C./h. The body color of the obtained phosphor was light green.

The $Ce^{3+}$-activated phosphor used in example 2 was a commercially available LuAG phosphor ($Lu_3Al_2Al_3O_{12}$: $Ce^{3+}$). In consideration of the fluorescence peak wavelength and the like, the chemical composition of the LuAG phosphor is estimated to be $(Lu_{0.995}Ce_{0.005})_3Al_2Al_3O_{12}$.

The obtained phosphor activated with $Cr^{3+}$ and the phosphor activated with $Ce^{3+}$ were mixed so that the weight ratio was 1:1 to obtain a mixed powder of example 2. A mortar and pestle were used for mixing, and the mixing time was 3 minutes.

[Evaluation]

(Crystal Structure Analysis)

The crystal structures of the $Cr^{3+}$-activated phosphor and the $Ce^{3+}$-activated phosphor used in example 1 were evaluated using an X-ray diffraction apparatus (X'Pert PRO; manufactured by Spectris Co., Ltd., PANalytical).

As a result of evaluation, it was found that the $Cr^{3+}$-activated phosphor and the $Ce^{3+}$-activated phosphor used in example 1 were mainly made from compounds with a garnet crystal structure, although the details are omitted. That is, both the $Cr^{3+}$-activated phosphor and the $Ce^{3+}$-activated phosphor used in example 1 were found to be garnet phosphors.

Next, the crystal structures of the $Cr^{3+}$-activated phosphor and the $Ce^{3+}$-activated phosphor used in example 2 were evaluated using an X-ray diffraction apparatus (X'Pert PRO; manufactured by Spectris Co., Ltd., PANalytical).

As a result of evaluation, it was found that the $Cr^{3+}$-activated phosphor and the $Ce^{3+}$-activated phosphor used in example 2 were mainly made from compounds with a garnet crystal structure, although the details are omitted. That is, both the $Cr^{3+}$-activated phosphor and the $Ce^{3+}$-activated phosphor used in example 2 were found to be garnet phosphors.

(Spectroscopic Property)

Next, the mixed powders of example 1 and example 2 were each laid in a stainless steel cylindrical folder having a diameter of 10 mm and a depth of 1 mm to form a wavelength converter, and the fluorescence spectral characteristics were evaluated. A quantum efficiency measurement system (QE-1100, manufactured by Otsuka Electronics Co., Ltd.) provided with an instantaneous multi-photometric system (MCPD-9800, manufactured by Otsuka Electronics Co., Ltd.) was used for the evaluation. The excitation wavelength was set to 450 nm.

Figure 12:
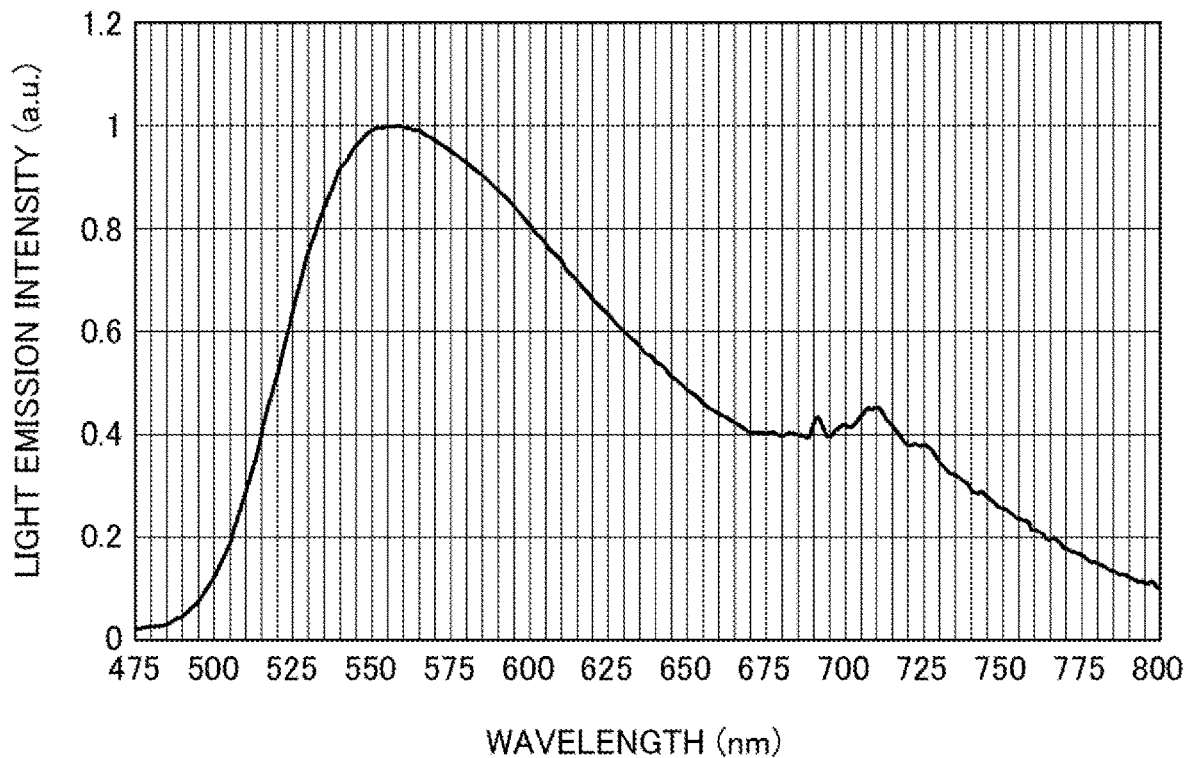
FIG. 12 is a spectrum of a light emitted by a wavelength converter according to a first example.

FIG. 12 illustrates the fluorescence spectrum of example 1. The fluorescence spectrum is normalized so that the maximum light emission intensity is 1. The fluorescence spectrum of example 1 was formed from a broad spectrum determined to be attributed to the $5d^1 \rightarrow 4f^1$ transition of $Ce^{3+}$ and a broad spectrum determined to be attributed to the d-d transition of $Cr^{3+}$. The peak wavelengths of respective spectra were 558 nm and 710 nm.

As is seen from FIG. 12, the fluorescence spectrum of example 1 has a less amount of a deep red light component, which becomes noise in the near-infrared light image sensor, than the conventional fluorescence spectrum. This is considered to be because the $Cr^{3+}$-activated phosphor strongly absorbed the light component in the deep red range among the fluorescent components of the $Ce^{3+}$-activated phosphor. It is not known that such an effect actually works, and it is demonstrated only by experimental verification.

In the fluorescence spectrum of example 1, the ratio of the minimum light emission intensity to the maximum light emission intensity was 39% in the wavelength range of 550 nm or more to 700 nm or less. This indicates that the wavelength converter of example 1 receives blue light and emits a fluorescence in which the ratio of the minimum light emission intensity to the maximum light emission intensity is 40% or less in the wavelength range of 550 nm or more to 700 nm or less.

Figure 13:
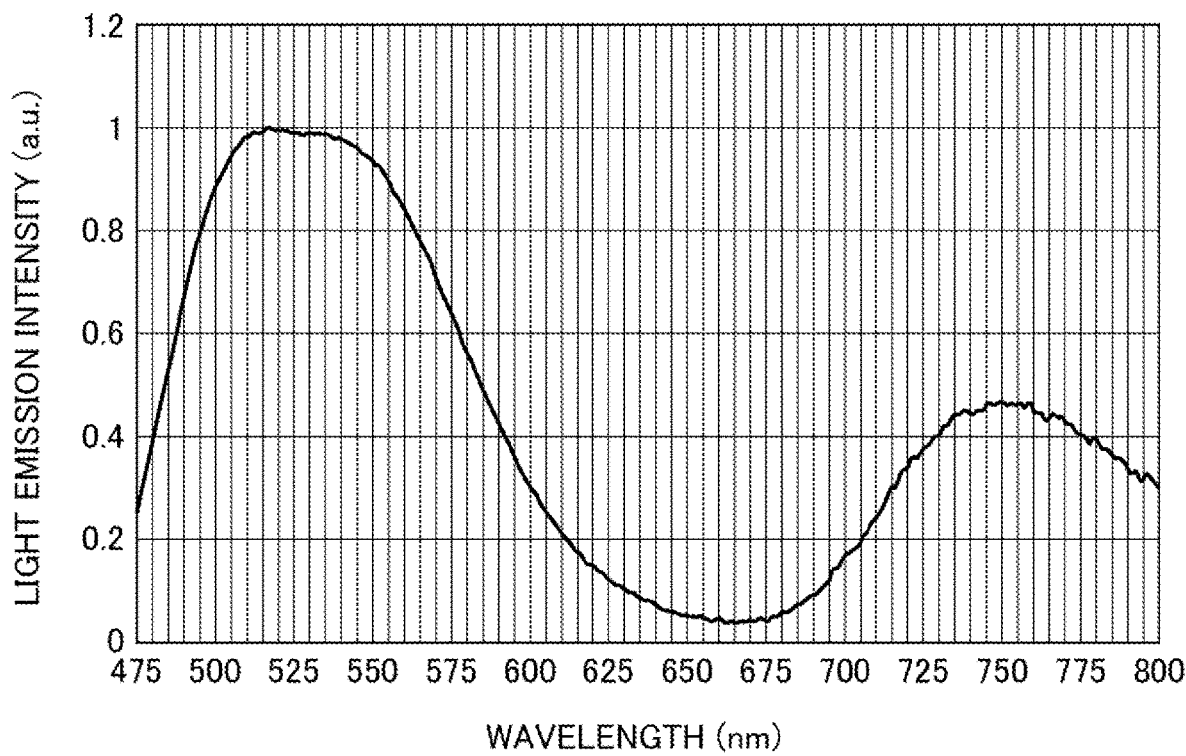
FIG. 13 is a spectrum of a light emitted by a wavelength converter according to a second example.

FIG. 13 illustrates the fluorescence spectrum of example 2. The fluorescence spectrum is normalized so that the maximum light emission intensity is 1. The fluorescence spectrum of example 2 was formed from a broad spectrum determined to be attributed to the $5d^1 \rightarrow 4f^1$ transition of $Ce^{3+}$ and a broad spectrum determined to be attributed to the d-d transition of $Cr^{3+}$. The peak wavelengths of respective spectra were 517 nm and 750 nm.

As is seen from FIG. 13, the fluorescence spectrum of example 2 has a less amount of a deep red light component, which becomes noise in the near-infrared light image sensor, than the conventional fluorescence spectrum. This is considered to be because the $Cr^{3+}$-activated phosphor strongly absorbed the light component in the deep red range among the fluorescent components of the $Ce^{3+}$-activated phosphor. It is not known that such an effect actually works, and it is demonstrated only by experimental verification.

In the fluorescence spectrum of example 2, the ratio of the minimum light emission intensity to the maximum light emission intensity was 4% in the wavelength range of 550 nm or more to 700 nm or less. This indicates that the wavelength converter of example 2 receives blue light and emits a fluorescence in which the ratio of the minimum light emission intensity to the maximum light emission intensity is 40% or less in the wavelength range of 550 nm or more to 700 nm or less.

The entire contents of Japanese Patent Application No. 2019-082925 (filed Apr. 24, 2019) are incorporated herein by reference.

Although the contents of the present embodiment have been described in accordance with the examples above, it is obvious to those skilled in the art that the present embodiment is not limited to these descriptions, and that various modifications and improvements are possible.

INDUSTRIAL APPLICABILITY

In accordance with the present disclosure, there is provided a wavelength converter capable of emitting a fluorescence spectrum in which a visible light fluorescent component and a near-infrared fluorescent component are sufficiently separated and the light emission intensity of a deep red light is relatively low, and a light emitting device, a medical system, an electronic apparatus and an inspection method using the wavelength converter.

REFERENCE SIGNS LIST

1 Wavelength converter
2 First phosphor
3 Second phosphor
5 Light source
10 Light emitting device
11 Endoscope (medical system)
101 Endoscope system (medical system)
114V Visible light image sensor (first image sensor)
114IR IR light image sensor (second image sensor)

The invention claimed is:
1. A wavelength converter, comprising:
a first phosphor activated with $Cr^{3+}$; and
a second phosphor activated with at least one ion of $Ce^{3+}$ or $Eu^{2+}$, wherein
a fluorescence spectrum of a fluorescence emitted by the second phosphor has a peak where a fluorescence intensity shows a maximum value in a wavelength range of 500 nm or more to less than 580 nm,
the wavelength converter emits a fluorescence having a light component over an entire range of 500 nm or more to less than 580 nm, and
the wavelength converter emits a light having a spectrum in which a ratio of a minimum light emission intensity to a maximum light emission intensity is 40% or less in a wavelength range of 550 nm or more to 700 nm or less,
wherein a wavelength having the maximum light emission intensity is 550 nm or more and less than 580 nm, and a wavelength having the minimum light emission intensity is 580 nm or more and 700 nm or less.
2. The wavelength converter according to claim 1, wherein a fluorescence spectrum of a fluorescence emitted by the first phosphor has a peak where a fluorescence intensity shows a maximum value in a wavelength range of 710 nm or more.

3. The wavelength converter according to claim 1 wherein the second phosphor is activated with $Ce^{3+}$.

4. A light emitting device, comprising:
   the wavelength converter according to claim 1; and
   a light source configured to emit a light that is wavelength-converted by the wavelength converter.

5. The light emitting device according to claim 4, wherein the light emitted by the light source is a laser light.

6. The light emitting device according to claim 5, wherein a spectrum of the light emitted by the light source has a peak where a intensity shows a maximum value in a wavelength range of 420 nm or more to less than 480 nm, and
   the light emitted by the light source is a blue light.

7. The light emitting device according to claim 6, wherein the light source includes a solid-state light emitting device, and
   the blue light is emitted by the solid-state light emitting device.

8. The light emitting device according to claim 4, wherein the light emitting device is a light source for a sensing system, or an illumination system for a sensing system.

9. A medical system, comprising:
   the light emitting device according to claim 4.

10. The medical system according to claim 9, wherein the medical system is used in either a fluorescence imaging method or a photodynamic therapy.

11. The medical system according to claim 9, further comprising:
    a first image sensor configured to detect reflected light of a visible light component emitted by the light emitting device; and
    a second image sensor configured to detect a fluorescent component of near infrared light emitted by a drug, wherein
    the drug is excited by a light emitted by the light emitting device.

12. An electronic apparatus, comprising:
    the light emitting device according to claim 4.

13. The electronic apparatus according to claim 12, wherein the electronic apparatus is any one of an information recognition device, a sorting device, a detection device, or an inspection device.

14. The electronic apparatus according to claim 13, wherein the inspection device is any one of a medical inspection device, an agricultural and livestock inspection device, a fishery inspection device, or an industrial inspection device.

15. An inspection method, comprising:
    using the light emitting device according to claim 4.

16. The light emitting device according to claim 4, wherein the light emitted by the light source is a continuous pulsed light.

17. An endoscope, comprising:
    the light emitting device according to claim 4.

* * * * *